United States Patent
Yao et al.

(10) Patent No.: US 11,292,777 B2
(45) Date of Patent: Apr. 5, 2022

(54) METHOD FOR PREPARING CYCLIC CARBONATE

(71) Applicant: SOOCHOW UNIVERSITY, Suzhou (CN)

(72) Inventors: Yingming Yao, Suzhou (CN); Liye Qu, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 678 days.

(21) Appl. No.: 16/316,616

(22) PCT Filed: Jan. 12, 2018

(86) PCT No.: PCT/CN2018/072305
§ 371 (c)(1),
(2) Date: Jan. 9, 2019

(87) PCT Pub. No.: WO2019/104841
PCT Pub. Date: Jun. 6, 2019

(65) Prior Publication Data
US 2021/0355094 A1    Nov. 18, 2021

(30) Foreign Application Priority Data
Nov. 30, 2017    (CN) .......................... 201711238580.8

(51) Int. Cl.
| | |
|---|---|
| *C07D 307/33* | (2006.01) |
| *B01J 31/22* | (2006.01) |
| *B01J 37/04* | (2006.01) |
| *B01J 37/08* | (2006.01) |
| *C07F 5/00* | (2006.01) |

(52) U.S. Cl.
CPC ........ *C07D 307/33* (2013.01); *B01J 31/2208* (2013.01); *B01J 31/2217* (2013.01); *B01J 37/04* (2013.01); *B01J 37/08* (2013.01); *C07F 5/003* (2013.01); *B01J 2231/321* (2013.01); *B01J 2531/0205* (2013.01); *B01J 2531/0238* (2013.01); *B01J 2531/26* (2013.01); *B01J 2531/36* (2013.01); *B01J 2531/38* (2013.01)

(58) Field of Classification Search
None
See application file for complete search history.

(56) References Cited

U.S. PATENT DOCUMENTS
6,924,379 B2    8/2005    Palanichamy et al.

FOREIGN PATENT DOCUMENTS
| | | |
|---|---|---|
| CN | 103254246 A | 8/2013 |
| CN | 103641811 A | 3/2014 |
| CN | 107827855 A | 3/2018 |
| WO | 2009014362 A2 | 1/2009 |

OTHER PUBLICATIONS

Wang et al. "Ambient chemical fixation of CO2 using a highly efficient heterometallic helicate catalyst system" Chemical Communications, 2018, vol. 54, pp. 2212-2215.*

* cited by examiner

*Primary Examiner* — Joseph R Kosack
(74) *Attorney, Agent, or Firm* — SZDC Law P.C.

(57) ABSTRACT

The present invention provides a method for preparing a cyclic carbonate, which has the advantages of high yield, mild reaction conditions, high catalytic efficiency under room temperature and 1 atm pressure conditions, and wide substrate scopes. It is not only suitable for monosubstituted epoxides, but also suitable for disubstituted epoxides. The method comprises the step of reacting epoxides of Formula (I) with carbon dioxide in the presence of a quaternary ammonium salt and a catalyst, to obtain a cyclic carbonate of Formula (II). The reaction formula is:

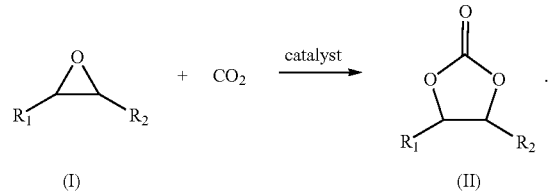

8 Claims, No Drawings

METHOD FOR PREPARING CYCLIC CARBONATE

This application is the National Stage Application of PCT/CN2018/072305, filed on Jan. 12, 2018, which claims priority to Chinese Application No. 201711238580.8, filed on Nov. 30, 2017, which is incorporated by reference for all purposes as if fully set forth herein.

FIELD OF THE INVENTION

The present invention relates to the technical field of preparation of organic compounds, and more particularly to a method for preparing a cyclic carbonate.

DESCRIPTION OF THE RELATED ART

Cyclic carbonates are a class of compounds with a wide range of applications. They can be used as electrolytes for lithium batteries, polymerizable monomers (for example, in synthesizing polyurethane) and intermediates for pharmaceutical synthesis. Therefore, the study of the synthesis of cyclic carbonates is of great significance and application value.

The conversion and utilization of carbon dioxide is one of the current research hotspots. As a greenhouse gas, the influence of carbon dioxide on the change of natural environment and climate has caused widespread social concern in recent years. Carbon dioxide is cheap, non-toxic, non-flammable, and rich in sources. By means of the conversion and utilization of carbon dioxide, the resourcelization of carbon dioxide is achieved, which not only solves the problem of greenhouse effect, but also turns the waste into value-added substances. In fact, carbon dioxide can be used as a valuable raw material in organic synthesis. Preparation of cyclic carbonates through the reaction of carbon dioxide with epoxides has attracted great attention, which is 100% atom economic, and conforms to the principle of green chemistry. Due to its high thermodynamic stability, reactions of carbon dioxide often require high temperature, high pressure and other harsh reaction conditions. Current studies have shown that adding certain amount of catalyst to the reaction system reduces the activation energy and increases the activity of the reaction. At present, there are many types of catalysts which are active in catalyzing the reaction of carbon dioxide with epoxides, mainly including some organic compounds, ionic liquids and metal complexes. Among these catalysts, organometallic compounds have been widely developed as catalysts.

In 2007, Michael North's research group reported that cyclic carbonates were prepared by catalytic reaction of carbon dioxide with styrene oxide in the presence of 2.5 mol % Al(Salen) compound and tetrabutylammonium bromide under room temperature and 1 atm $CO_2$ pressure conditions. The yield was up to 98% after reacting for 24 h. However, the catalyst loading is large (up to 2.5 mol %), which is less active or inactive for the sterically hindered disubstituted epoxides (J. Meléndez, M. North, and R. Pasquale, Eur. J. Inorg. Chem., 2007, 3323). In 2010, Arjan W. Kleij's research group reported that Zn(Salphen) compound and tetrabutylammonium iodide catalyzed reaction of carbon dioxide (10 atm) with 1,2-epoxyhexane in dichloromethane at 45° C. The yield was up to 80% after 18 h reaction. This reaction required toxic dichloromethane as solvent, and is not active for disubstituted epoxides (A. Decortes, M. M. Belmonte, J. Benet-Buchholz and A. W. Kleij, Chem. Commun., 2010, 46, 4580). In 2013, Arjan W. Kleij et al. reported that Al complex bearing an amine-bridged tri(phenolate) ligand and tetrabutylammonium iodide catalyzed reaction of carbon dioxide (10 atm) with propylene oxide at 90° C., which gave yields of up to 96% after 2 h reaction. Although this catalytic system showed good catalytic activity, synthesis and separation of the ligand used in the catalyst are complex, and the yield is only 21% (C. J. Whiteoak, N. Kielland, V. Laserna, E. C. Escudero-Adán, E. Martin and A. W. Kleij, J. Am. Chem. Soc., 2013, 135, 1228). In 2016, Pereira et al. reported that in the presence of 0.07 mol% of a manganese compound bearing porphyrin ligand, cyclic carbonates were obtained from catalytic reaction of styrene oxide with carbon dioxide at a temperature of 80° C., where the yield is 52%. In this catalytic system, the catalyst loading is low, but a high pressure of 50 atm is required (Laia Cuesta-Aluja, Javier Castilla, Anna M. Masdeu-Bultó, César A. Henriques, Mário J. F. Calvete, Mariette M. Pereira Journal of Molecular Catalysis A: Chemical, 2016, 489).

At present, although many methods for preparing cyclic carbonates are available, they suffer from some disadvantages, such as requirements of high pressure (greater than 10 atm), high temperature (greater than 100° C.), and toxic solvent (such as dichloromethane) in the reaction, multi-step and low-yielding catalyst synthesis. Moreover, most catalytic systems are applicable to a narrow range of substrates, and show low or even no activity to disubstituted epoxides. Therefore, it is of great significance to develop a method for synthesizing cyclic carbonates that is applicable to a wide range of substrates, working under mild conditions, and meeting the requirements of green chemistry. Previously, an invention was made by Yao Yingming, Qin Jie and others from our research group, in which a rare earth metal complex is used as a catalyst to effectively catalyze the reaction of carbon dioxide with epoxides to form cyclic carbonates. However, the reaction requires a temperature of 85° C. (Patent Application CN201310708187 and CN103641811A). Improvements and modification are made in the present invention based on this, to achieve the conversion of most of epoxides with carbon dioxide at room temperature and 1 atm $CO_2$ pressure conditions.

SUMMARY OF THE INVENTION

An object of the present invention is to provide a method for preparing a cyclic carbonate, and the method has the advantages of high yield, mild reaction conditions, high catalytic efficiency under room temperature and 1 atm $CO_2$ pressure conditions, as well as wide substrate scopes. This protocol is not only suitable for monosubstituted epoxides, but also suitable for disubstituted epoxides.

For the above purpose, the following technical solution is adopted in the present invention.

A method for preparing a cyclic carbonate, comprises the steps of: reacting an epoxide of Formula (I) with carbon dioxide in the presence of a quaternary ammonium salt and a catalyst, to obtain a cyclic carbonate of Formula (II), the reaction formula is as follows:

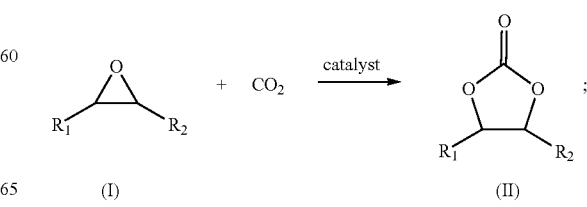

and the catalyst is an ethylenediamino bridged tetra(phenolate) rare earth-zinc heterobimetallic compound of Formula (III):

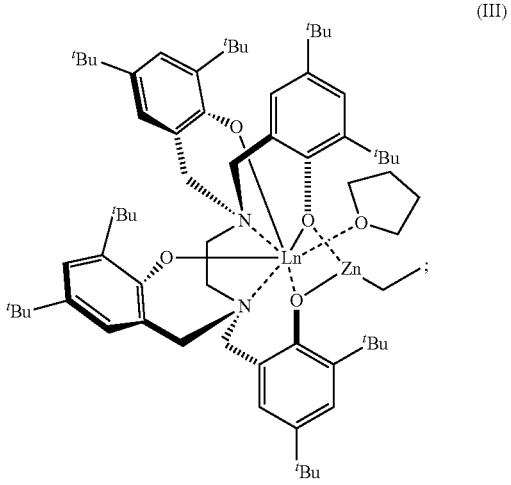

(III)

wherein:

$R_1$ and $R_2$ are independently selected from the group consisting of hydrogen, alkyl, alkoxy, aryl and an ester group; or $R_1$ and $R_2$ are independently selected from alkyl and alkoxy, and $R_1$ and $R_2$, together with the atoms to which they are attached, form a ring;

Ln is a rare earth metal ion.

Preferably, the rare earth metal is yttrium, ytterbium or samarium.

More preferably, the rare earth metal is yttrium.

Preferably, the quaternary ammonium salt is selected from the group consisting of tetrabutylammonium iodide, tetrabutylammonium bromide, tetraoctylammonium bromide, bis(triphenylphosphine)ammonium chloride and any combination thereof.

More preferably, the molar amount of the quaternary ammonium salt is 3-4 times the amount of the bridged tetra(phenolate) rare earth metal compound.

More preferably, the molar amount of the quaternary ammonium salt is 0.8-4% of that of the reactant epoxide.

Preferably, the alkyl group is a substituted or non-substituted linear or branched $C_{1-18}$ alkyl group.

More preferably, the alkyl group is substituted or non-substituted methyl, ethyl, propyl, isopropyl, butyl, isobutyl, sec-butyl, tert-butyl, pentyl, isopentyl, tert-pentyl, hexyl, heptyl, octyl, nonyl, decyl, undecyl, dodecyl, hexadecyl, or octadecyl group.

Preferably, the alkoxy group is a substituted or non-substituted linear or branched $C_{1-18}$ alkyl group.

More preferably, the alkoxy group is methoxy, ethoxy, propoxy, isopropoxy, butoxy, isobutoxy, tert-butoxy, sec-butoxy, pentyloxy, hexyloxy, hpeptyloxy, decyloxy, dodecyloxy, hexadecyloxy or octadecyloxy group.

Preferably, the aryl group is a substituted or non-substituted $C_{6-14}$ aryl group.

More preferably, the aryl group is phenyl, alkylphenyl, alkoxyphenyl, benzyl, alkylbenzyl, alkoxybenzyl or naphthyl group.

Preferably, the ester group is —COO—$R_3$, where $R_3$ is H, $C_{1-10}$ alkyl or aryl.

More preferably, the ester group is —COO—$R_3$, where $R_3$ is H, methyl, ethyl, propyl, isopropyl, butyl, isobutyl, sec-butyl, tert-butyl, pentyl, isopentyl, tert-pentyl, hexyl, heptyl, octyl, nonyl, decyl, phenyl or benzyl group.

Preferably, the alkyl, alkoxy, or aryl group bears one or more substituent(s) that is/are nitro, cyano, hydroxyl, or halo group, in which the halo is fluoro, chloro, bromo, or iodo group.

Preferably, the alkyl, alkoxy, or aryl group bears one or more substituent(s) that is/are halo, in which the halo is fluoro, chloro, bromo, or iodo group.

Preferably, $R_1$ and $R_2$ are independently selected from alkyl and alkoxy group, and $R_1$ and $R_2$, together with the atoms to which they are attached, form a ring.

More preferably, $R_1$ and $R_2$ are independently selected from alkyl and alkoxy group, and $R_1$ and $R_2$, together with the atoms to which they are attached, form a $C_{3-18}$ carbocyclic ring or a $C_{2-17}$ heterocyclic ring containing oxygen.

Still more preferably, $R_1$ and $R_2$ are independently selected from alkyl and alkoxy group, and $R_1$ and $R_2$, together with the atoms to which they are attached, form a $C_{3-7}$ carbocyclic ring or a $C_{2-6}$ heterocyclic ring containing oxygen atom.

More preferably, $R_1$ and $R_2$ are independently selected from alkyl and alkoxy group, and $R_1$ and $R_2$, together with the atoms to which they are attached, form cyclopropane, cyclobutane, cyclopentane, cyclohexane, cycloheptane, oxirane, oxetane, oxolane, oxane, oxolane or oxepane.

Preferably, the temperature of the reaction for producing the cyclic carbonate is 25-90° C.

Preferably, the time of the reaction for producing the cyclic carbonate is 24-40 h.

Preferably, the pressure of the carbon dioxide is 1-10 atm.

Preferably, the molar ratio of the bridged tetra(phenolate) rare earth-zinc heterobimetallic compound to the epoxide of Formula (I) is 1:100-500.

Moe preferably, the molar ratio of the bridged tetra (phenolate) rare earth-zinc heterobimetallic compound to the epoxide of Formula (I) is 1:100.

Preferably, the method for preparing cyclic carbonates comprises the steps of:

1) adding the bridged tetra(phenolate) rare earth-zinc heterobimetallic compound, the quaternary ammonium salt and the epoxide to a reactor, and then introducing carbon dioxide for reaction; and 2) after the reaction is completed, purifying the reaction product by column chromatography, to obtain a pure product.

More preferably, the catalyst ethylenediamino bridged tetra(phenolate) rare earth-zinc heterobimetallic compound is synthesized by the steps of:

1) synthesis of ethylenediamino bridged tetra(phenol) $LH_4$: adding ethylenediamine, formaldehyde and 2,4-di-tert-butylphenol to a reactor at a molar ratio of 1:4:6-1:4:8; heating the mixture at 75-85° C. for 60-72 h in the absence of a solvent; After reaction, adding methanol and ultrasonicating the mixture, which gives a white suspension that is filtered and dried to give $LH_4$ as a white solid, where the reaction formula is:

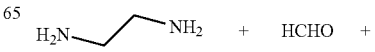 + HCHO +

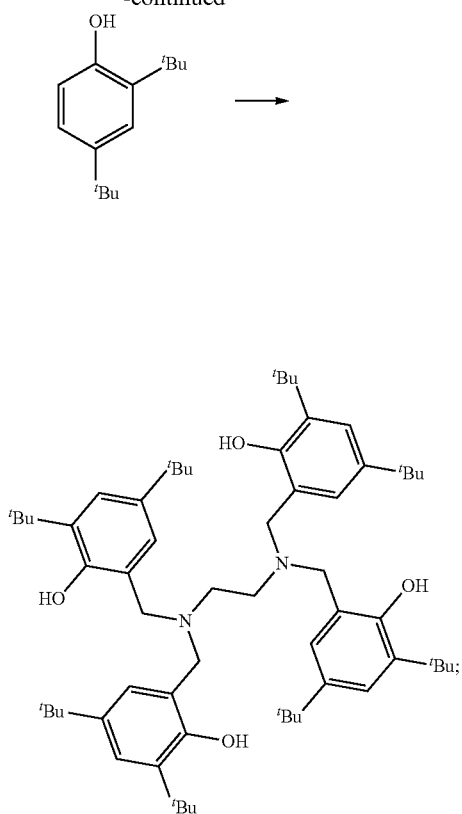

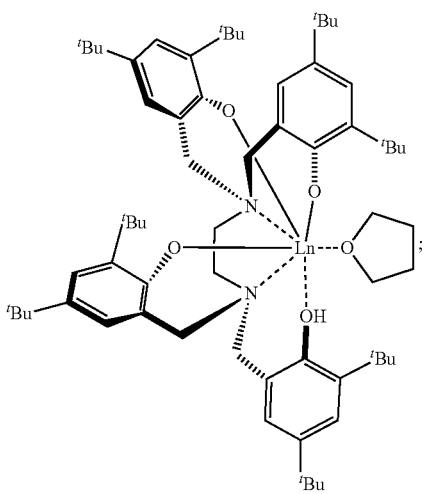

2) synthesis of bridged tetra(phenolate) rare earth metal compound LLn(THF): reacting the ethylenediamino bridged tetra(phenol) with LnCp3(THF) at a molar ratio of 1:1-1:1.05 for 5-12 h in an ether solvent in the absence of water and oxygen under an inert atmosphere, where the reaction temperature is 20-50° C., and not higher than the boiling point of the solvent; and then removing the solvent, extracting the residue with a hydrocarbon solvent, centrifuging the extracted product, discarding the precipitate, and concentrating the supernatant to obtain the LLn(THF) crystal, where the reaction formula is:

3) synthesis of bridged tetra(phenolate) rare earth-zinc heterobimetallic compound LnZnL(THF): adding a solution of diethyl zinc in hexane or toluene to a reactor in the absence of water and oxygen under an inert atmosphere, slowly adding a solution of LnL(THF) in tetrahydrofuran dropwise at −5-0° C. at a molar ratio of 1:1-1.05:1, and after addition, reacting for 8-12 h at a reaction temperature of 25-50° C.; and then removing the solvent, extracting the residue with an ether solvent, centrifuging the extracted product, discarding the precipitate, and concentrating the supernatant to obtain the LnZnL(THF) crystal, where the reaction formula is:

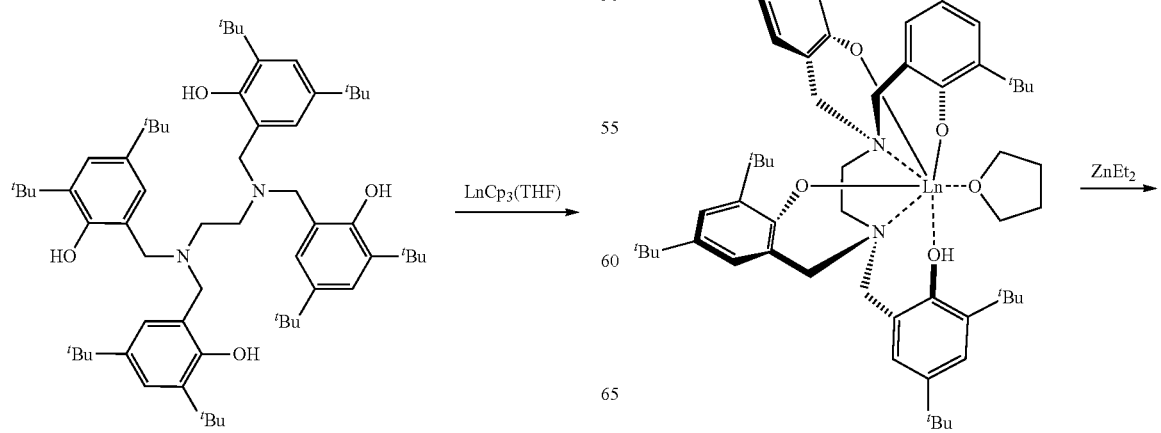

-continued

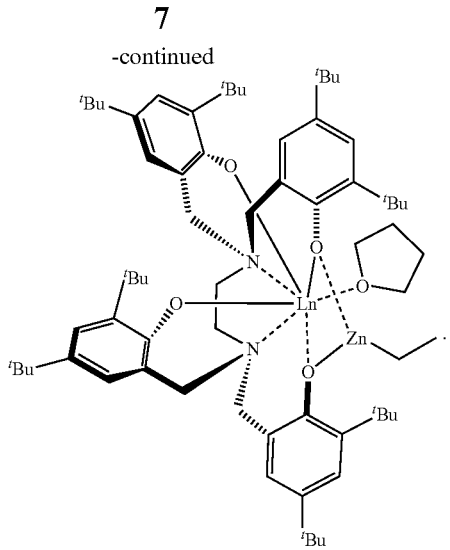

Preferably, the ether solvent is tetrahydrofuran or diethyl ether; and the hydrocarbon solvent is hexane or toluene.

In the invention, the general chemical formula of the bridged tetra(phenolate) rare earth metal compound is LnZnL(THF), where L denotes the ethylenediamino bridged tetra(phenolate) ligand; THF is tetrahydrofuran; Zn is zinc; Ln denotes a rare earth metal ion, selected from yttrium, ytterbium and samarium, and preferably yttrium.

By means of the above technical solutions, the invention has the following advantages as compared with the prior art:

1. The catalyst bridged tetra(phenolate) rare earth-zinc heterobimetallic compound used in the invention has the advantages of definite structure, high yield, simple separation and purification; and the quaternary ammonium salt is widely available.

2. The catalyst disclosed in the present invention has high activity and is efficient under mild reaction conditions. The addition reaction of epoxide with carbon dioxide can be catalyzed effectively in the presence of a small amount of catalyst and quaternary ammonium salt under the reaction conditions of 25° C. and carbon dioxide pressure of 1 atm. When the molar amount of the catalyst is 1 mol % of the reactant epoxide, and the molar amount of the quaternary ammonium salt is 3% of the reactant epoxide, the yield of the product reaches 96%. Furthermore, mild conditions are favorable for the industry application of the reaction.

3. The preparation method disclosed in the invention has the advantages of readily available raw materials, mild reaction conditions, and wide substrate scopes, which is applicable not only to monosubstituted epoxides, but is also to disubstituted epoxides. The reaction time is short, the yield of the target product is high, and the experiment procedure and the work-up process are simple.

DETAILED DESCRIPTION OF THE PREFERRED EMBODIMENTS

The invention will be further illustrated in more detail with reference to the accompanying drawings and embodiments. It is noted that, the following embodiments only are intended for purposes of illustration, but are not intended to limit the scope of the present invention.

Embodiment 1

Preparation of bridged tetra(phenolate) rare earth metal compound YbL(THF):

(1) $LH_4$ (2.80 g, 3.00 mmol) was dissolved in tetrahydrofuran, which was added to a solution of $YCp_3$(THF) (1.31 g, 3.00 mmol) in tetrahydrofuran. The resulting solution was left for 4 h under stirring at room temperature, which gave a clear yellow solution.

(2) The solvent was removed, and hexane (10 mL) and tetrahydrofuran (0.5 mL) were added. The resulting solution was heated at 60° C., and centrifuged. The supernatant was transferred and allowed to stand at room temperature until yellow crystals (2.82 g, 2.39 mmol) precipitated (yield 80%). Melting point: 188-190° C. Element analysis: C, 67.50; H, 8.94; N, 2.47. IR spectrum (KBr, $cm^{-1}$): 3423(s), 2960(w), 2904(s), 2869(s), 1603(s), 1479(s), 1442(s), 1411(s), 1362(s), 1304(s), 1282(s), 1238(s), 1204(s), 1166(s), 1132(s), 1026(s), 973(s), 912(s), 877(s), 833(s), 806(s), 759(s), 745(s), 671(s), 529(s), 458(s).

Embodiment 2

Preparation of Bridged Tetra(Phenolate) Rare Earth Metal Compound YL(THF):

(1) $LH_4$ (2.80 g, 3.00 mmol) was dissolved in tetrahydrofuran, which was added to a solution of $YCp_3$(THF) (1.07 g, 3.00 mmol) in tetrahydrofuran. The resulting solution was left for 4 h under stirring at room temperature, which gave a clear pale yellow solution.

(2) The solvent was removed, and toluene (15 mL) and tetrahydrofuran (0.5 mL) were added. The resulting solution was heated at 60° C., and centrifuged. The supernatant was transferred and allowed to stand at room temperature until colorless crystals (2.59 g, 2.37 mmol) precipitated (yield 79%). Melting point: 178-180° C. Element analysis: C, 72.59; H, 9.65; N, 2.62. IR spectrum (KBr, 3437(s), 2953 (w), 2904(s), 2867(s), 1603(s), 1479(s), 1442(s), 1414(s), 1362(s), 1304(s), 1271(s), 1238(s), 1202(s), 1167(s), 1132(s), 1108(s), 974(s), 912(s), 875(s), 837(s), 805(s), 770(s), 744(s), 669(s), 533(s), 457(s). $^1$1-1 NMR spectrum ($C_6D_6$, δ): 7.52 (s, 4H, ArH), 6.93 (s, 4H, ArH) 4.32 (s, 4H, $ArCH_2N$), 4.10 (br, 4H, $ArCH_2N$), 2.93 (br, s, 4H, N—$CH_2$—$CH_2$—N), 1.53-1.36 (m, 72H, $C(CH_3)_3$).

Embodiment 3

Preparation of Bridged Tetra(phenolate) Rare Earth Metal Compound SmL(THF):

(1) $LH_4$ (2.80 g, 3.00 mmol) was dissolved in tetrahydrofuran, which was added to a solution of $SmCp_3$(THF) (1.25 g, 3.00 mmol) in tetrahydrofuran. The resulting solution was left for 4 h under stirring at room temperature, which gave a clear yellow solution.

(2) The solvent was removed, and hexane (14 mL) and tetrahydrofuran (0.5 mL) were added. The resulting solution was heated at 60° C., and centrifuged. The supernatant was transferred and allowed to stand at room temperature until yellow crystal (2.50 g, 2.16 mmol) precipitated (yield 72%). Melting point: 199-201° C. Element analysis: C, 68.52; H, 8. 69; N, 2.53. IR spectrum (KBr, $cm^{-1}$): 3423(s), 2960(w), 2904(s), 2869(s), 1603(s), 1477(s), 1440(s), 1414(s), 1362(s), 1301(s), 1276(s), 1240(s), 1202(s), 1167(s), 997(s), 969(s), 959(s), 913(s), 875(s), 833(s), 808(s), 770(s), 741(s), 691(s), 523(s), 435(s).

Embodiment 4

Preparation of Bridged Tetra(phenolate) Rare Earth-Zinc Heterobimetallic Compound ZnYL(THF):

(1) YL(THF) (3.27 g, 3.00 mmol) was dissolved in tetrahydrofuran, which was added to a solution of 3 mL diethyl zinc in hexane (1 mol/L). The resulting solution was left for 10 h under stirring at room temperature, which gave a clear yellow solution.

(2) The solvent was removed, and tetrahydrofuran (15 mL) was added. The resulting solution was heated at 60° C., and centrifuged. The supernatant was transferred and allowed to stand at room temperature until colorless crystal (2.59 g, 2.16 mmol) precipitated (yield 72%). Melting point: 205-207° C. Element analysis: C, 68.78; H, 9.00; N, 2.37. IR spectrum (KBr, cm$^{-1}$): 3442(s), 2953(w), 2904(s), 2866(s), 1604(s), 1476(s), 1444(s), 1414(s), 1361(s), 1309(s), 1232(s), 1204(s), 1168(s), 1130(s), 1059(s), 1018(s), 972(s), 916(s), 872(s), 836(s), 803(s), 776(s), 745(s), 672(s), 613(s), 524(s), 444(s).

Embodiment 5

Catalytic Reaction of 1,2-Epoxyhexane with Carbon Dioxide in the Presence of 0.2% ZnYL(THF) and 0.8% Tetrabutylammonium Bromide To a reaction flask, 1,2-epoxyhexane (2 mL, 0.0164 mol), ZnYL(THF) (0.0398 g, 3.36×10$^{-5}$ mol), and tetrabutylammonium bromide (0.0443 g, 1.33×10$^{-4}$ mol) were added, and a balloon containing carbon dioxide was connected. The reaction was heated for 24 h in an oil bath at 40° C. After reaction, a sample was taken and the yield was determined as 81% after analyzing by $^1$H NMR spectroscopy.

Embodiment 6

Catalytic Reaction of 1,2-Epoxyhexane with Carbon Dioxide in the Presence of 0.2% ZnYL(THF) and 0.8% Tetraoctylammonium Bromide To a reaction flask, 1,2-epoxyhexane (2 mL, 0.0164 mol), ZnYL(THF) (0.0398 g, 3.36×10$^{-5}$ mol), and tetraoctylammonium bromide (0.0728 g, 1.33×10$^{-4}$ mol) were added, and a balloon containing carbon dioxide was connected. The reaction was heated for 24 h in an oil bath at 40° C. Then the reaction flask was cooled in an ice bath, and the remaining carbon dioxide gas was discharged. A sample was taken and the yield was determined as 63% after analyzing by $^1$H NMR spectroscopy.

Embodiment 7

Catalytic Reaction of 1,2-Epoxyhexane with Carbon Dioxide in the Presence of 0.2% ZnYL(THF) and 0.8% Tetrabutylammonium Iodide To a reaction flask, 1,2-epoxyhexane (2 mL, 0.0164 mol), ZnYL(THF) (0.0398 g, 3.36×10$^{-5}$ mol), and tetrabutylammonium iodide (0.0518 g, 1.33×10$^{-4}$ mol) were added, and a balloon containing carbon dioxide was connected. The reaction was heated for 24 h in an oil bath at 40° C. Then the reaction flask was cooled in an ice bath, and the remaining carbon dioxide gas was discharged. A sample was taken and the yield was determined as 51% after analyzingby $^1$HNMR spectroscopy.

Embodiment 8

Catalytic Reaction of 1,2-Epoxyhexane with Carbon Dioxide in the Presence of 1% ZnYL(THF) and 4% Tetrabutylammonium Bromide To a reaction flask, 1,2-epoxyhexane (2 mL, 0.0164 mol), ZnYL(THF) (0.1942 g, 1.64×10$^{-4}$ mol), and tetrabutylammonium bromide (0.2180 g, 6.56×10$^{-4}$ mol) were added, and a balloon containing carbon dioxide was connected. The reaction was continued for 24 h in an oil bath at 25° C. The remaining carbon dioxide gas was discharged. A sample was taken and the yield was determined as 98% after analyzing by $^1$H NMR spectroscopy.

Embodiment 9

Catalytic Reaction of 1,2-Epoxyhexane with Carbon Dioxide in the Presence of 0.5% ZnYL(THF) and 2% Tetrabutylammonium Bromide To a reaction flask, 1,2-epoxyhexane (2 mL, 0.0164 mol), ZnYL(THF) (0.0971 g, 8.20×10$^{-5}$ mol), and tetrabutylammonium bromide (0.1057 g, 3.28×10$^{-4}$ mol) were added, and a balloon containing carbon dioxide was connected. The reaction was continued for 24 h in an oil bath at 25° C. The remaining carbon dioxide gas was discharged. A sample was taken and the yield was determined as 76% after analyzing by $^1$H NMR spectroscopy.

Embodiment 10

Catalytic Reaction of 1,2-Epoxyhexane with Carbon Dioxide in the Presence of 1% ZnYL(THF) and 3% Tetrabutylammonium Bromide To a reaction flask, 1,2-epoxyhexane (2 mL, 0.0164 mol), ZnYL(THF) (0.1942 g, 1.64×10$^{-4}$ mol), and tetrabutylammonium bromide (0.1586 g, 4.92×10$^{-4}$ mol) were added, and a balloon containing carbon dioxide was connected. The reaction was continued for 24 h in an oil bath at 25° C. The remaining carbon dioxide gas was discharged. A sample was taken and the yield was determined as 96% after analyzing by $^1$H NMR spectroscopy.

Embodiment 11

Catalytic Reaction of 1,2-Epoxypropyl p-tert-butylbenzoate with Carbon Dioxide in the Presence of 1% ZnYL(THF) and 3% Tetrabutylammonium Bromide:

To a reaction flask, 1,2-epoxypropyl p-tert-butylbenzoate (2 mL, 0.0092 mol), ZnYL(THF) (0.1087 g, 9.20×10$^{-5}$ mol), and tetrabutylammonium bromide (0.0914 g, 2.76×10$^{-4}$ mol) were added, and a balloon containing carbon dioxide was connected. The reaction was continued for 40 h in an oil bath at 25° C. The remaining carbon dioxide gas was discharged. The reaction solution was mixed with dichloromethane (5 mL), and the product was isolated by flask column chromatography as a white solid (2.06 g, yield 80%).

Embodiment 12

Catalytic Reaction of 1,2-epoxydodecane with Carbon Dioxide in the Presence of 1% ZnYL(THF) and 3% Tetrabutylammonium Bromide To a reaction flask, 1,2-epoxycyclododecane (1.8 mL, 0.0083 mol), ZnYL(THF) (0.0981 g, 8.30×10$^{-5}$ mol), and tetrabutylammonium bromide (0.0825 g, 2.49×10$^{-4}$ mol) were added, and a balloon containing carbon dioxide was connected. The reaction was continued for 40 h in an oil bath at 25° C. The reaction solution was mixed with dichloromethane (5 mL), and the product was isolated by flask column chromatography as a white solid (1.78 g, yield 94%).

Embodiment 13

Catalytic Reaction of Epichlorohydrin with Carbon Dioxide in the Presence of 1% ZnYL(THF) and 3% Tetrabutylammonium Bromide To a reaction flask, epichlorohydrin (1 mL, 0.0127 mol), ZnYL(THF) (0.1512 g, $1.27 \times 10^{-4}$ mol), and tetrabutylammonium bromide (0.1266 g, $3.81 \times 10^{-4}$ mol) were added, and a balloon containing carbon dioxide was connected. The reaction was continued for 24 h in an oil bath at 25° C. The reaction solution was mixed with dichloromethane (3 mL), the product was isolated by flask column chromatography as a colorless oil (1.21 g, yield 70%).

Embodiment 14

Catalytic Reaction of Styrene Oxide with Carbon Dioxide in the Presence of 1% ZnYL(THF) and 3% Tetrabutylammonium Bromide To a reaction flask, styrene oxide (1 mL, 0.0084 mol), ZnYL(THF) (0.0992 g, $8.40 \times 10^{-5}$ mol), and tetrabutylammonium bromide (0.0835 g, $2.52 \times 10^{-4}$ mol) were added, and a balloon containing carbon dioxide was connected. The reaction was continued for 24 h in an oil bath at 25° C. The reaction solution was mixed with dichloromethane (3 mL), the product was isolated by flask column chromatography as a white solid (1.16 g, yield 84%).

Embodiment 15

Catalytic Reaction of 2,3-epoxypropyl n-propyl Ether with Carbon Dioxide in the Presence of 1% ZnYL(THF) and 3% Tetrabutylammonium Bromide To a reaction flask, 2,3-epoxypropyl n-propyl ether (1.8 mL, 0.0152 mol), ZnYL(THF) (0.1795 g, $1.52 \times 10^{-4}$ mol), and tetrabutylammonium bromide (0.1511 g, $4.56 \times 10^{-4}$ mol) were added, and a balloon containing carbon dioxide was connected. The reaction was continued for 24 h in an oil bath at 25° C. The reaction solution was mixed with dichloromethane (5 mL), the product was isolated by flask column chromatography as a white solid (1.69 g, yield 84%).

Embodiment 16

Catalytic Reaction of Cyclopentene Oxide with Carbon Dioxide in the Presence of 1% ZnYL(THF) and 3% Tetrabutylammonium Bromide To a reaction flask, cyclopentene oxide (1.8 mL, 0.0206 mol), ZnYL(THF) (0.1795 g, $2.06 \times 10^{-4}$ mol), and tetrabutylammonium bromide (0.1511 g, $6.18 \times 10^{-4}$ mol) were added. The mixed solution was added to a high-pressure reactor, which was sealed and into which 10 atm of carbon dioxide was then introduced. The reaction was continued for 24 h in an oil bath at 70° C. The reactor was cooled in an ice bath. The reaction solution was mixed with dichloromethane (5 mL), and the product was isolated by flask column chromatography as a colorless oil (2.32 g, yield 88%).

Embodiment 17

Catalytic Reaction of Stilbene Oxide with Carbon Dioxide in the Presence of 1% ZnYL(THF) and 3% Tetrabutylammonium Bromide To a reaction flask, stilbene oxide (1 g, 0.0050 mol), the solvent n-butyl ketone (2 mL), ZnYL(THF)(0.0435 g, $5.01 \times 10^{-5}$ mol), and tetrabutylammonium bromide (0.0498 g, $1.50 \times 10^{-4}$ mol) were added. The mixed solution was added to a high-pressure reactor, which was sealed and into which 10 atm of carbon dioxide was then introduced. The reaction was continued for 40 h in an oil bath at 90° C. After reaction, the reactor was cooled in an ice bath. The product was isolated by flask column chromatography as a white solid (0.60 g, yield 50%).

Embodiment 18

Catalytic Reaction of 1,2-epoxytetrahydrofuran with Carbon Dioxide in the Presence of 1% ZnYL(THF) and 3% Tetrabutylammonium Bromide To a reaction flask, 1,2-epoxytetrahydrofuran (0.8602 g, 0.0101 mol), ZnYL(THF) (0.0871 g, $1.00 \times 10^{-4}$ mol), and tetrabutylammonium bromide (0.0996 g, $3.01 \times 10^{-4}$ mol) were added. The mixed solution was added to a high-pressure reactor, which was sealed and into which 10 atm of carbon dioxide was then introduced. The reaction was continued for 24 h in an oil bath at 70° C. After reaction, the reactor was cooled in an ice bath. The product was isolated by flask column chromatography as a white solid (1.20 g, yield 92%).

The above description is only preferred embodiments of the present invention and not intended to limit the present invention. It should be noted that those of ordinary skill in the art can further make various modifications and variations without departing from the technical principles of the present invention, and these modifications and variations also should be considered to be within the scope of protection of the present invention.

What is claimed is:

1. A method for preparing a cyclic carbonate, comprising a step of:

reacting an epoxide of Formula (I) with carbon dioxide in the presence of a quaternary ammonium salt and a catalyst, to obtain a cyclic carbonate of Formula (II), the reaction formula being:

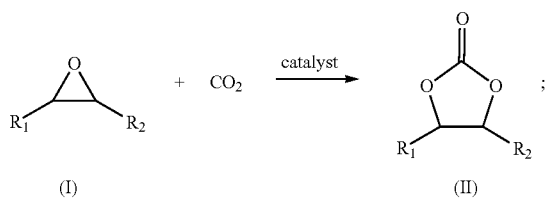

and the catalyst being an ethylenediamino bridged tetra(phenolate) rare earth-zinc heterobimetallic compound of Formula (III),

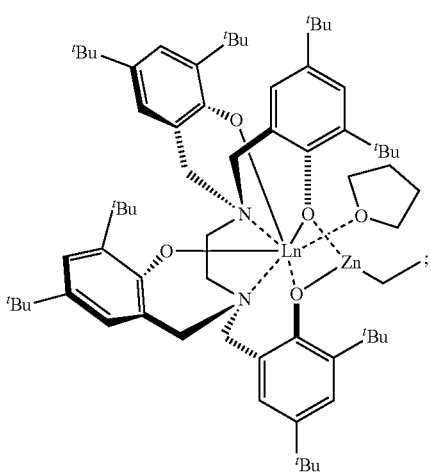

(III)

wherein:

$R_1$ and $R_2$ are independently selected from the group consisting of hydrogen, an alkyl, alkoxy, aryl and ester group; or $R_1$ and $R_2$ are independently selected from alkyl and alkoxy, and $R_1$ and $R_2$, together with the atoms to which they are attached, form a ring;

Ln is yttrium, ytterbium or samarium;

wherein the quaternary ammonium salt is selected from the group consisting of tetrabutylammonium iodide, tetrabutylammonium bromide, tetraoctylammonium bromide, bis(triphenylphosphine)ammonium chloride and any combination thereof; and wherein a molar amount of the quaternary ammonium salt is 3-4 times a molar amount of the ethylenediamino bridged tetra(phenolate) rare earth-zinc heterobimetallic compound of formula (III).

2. The method for preparing a cyclic carbonate as claimed in claim 1, wherein the alkyl group is a substituted or non-substituted linear or branched $C_{1-18}$ alkyl group, and the alkoxy group a substituted or non-substituted linear or branched $C_{1-18}$ alkoxy group.

3. The method for preparing a cyclic carbonate as claimed in claim 1, wherein the aryl group is a substituted or non-substituted $C_{6-14}$ aryl group; and the ester group is —COO—$R_3$, in which $R_3$ is H, $C_{1-10}$ alkyl or aryl group.

4. The method for preparing a cyclic carbonate as claimed in claim 2, wherein the alkyl, alkoxy, or aryl group has one or more substituent(s) that is/are nitro, cyano, hydroxyl or halo, in which the halo is fluoro, chloro, bromo or iodo.

5. The method for preparing a cyclic carbonate as claimed in claim 1, wherein:

$R_1$ and $R_2$, together with the atoms to which they are attached, form a $C_{3-18}$ carbocyclic ring or a $C_{2-17}$ heterocyclic ring containing an oxygen atom.

6. The method for preparing a cyclic carbonate as claimed in claim 1, wherein the temperature of addition reaction is 25-90° C.

7. The method for preparing a cyclic carbonate as claimed in claim 1, wherein a molar ratio of the bridged tetra (phenolate) rare earth-zinc heterobimetallic compound to the epoxide of Formula (I) is 1:100-500.

8. The method for preparing a cyclic carbonate as claimed in claim 1, wherein the catalyst of ethylenediamino bridged tetra(phenolate) rare earth-zinc heterobimetallic compound is synthesized by steps of:

1) synthesis of ethylenediamino bridged tetra(phenol) $LH_4$: heating ethylenediamine, formaldehyde and 2,4-di-tert-butylphenol at 75-85° C. for 60-72 h to obtain the ethylenediamino bridged tetra(phenol) $LH_4$, wherein the molar ratio of ethylenediamine, formaldehyde and 2,4-di-tert-butylphenol is 1:4:6-1:4:8; and the reaction formula is:

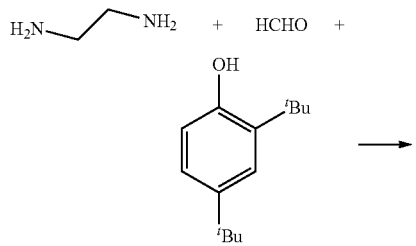

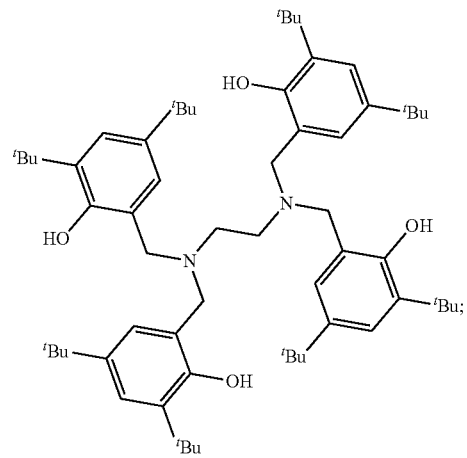

2) synthesis of bridged tetra(phenolate) rare earth metal compound LLn (THF): reacting the ethylenediamino bridged tetra(phenol) with $LnCp_3$(THF) in ether at 20-50 ° C. for 4-12 h in the absence of water and oxygen, to obtain the bridged tetra(phenolate) rare earth metal compound LLn(THF), wherein the molar ratio of the ethylenediamino bridged tetra(phenol) to $LnCp_3$(THF) is 1:1-1:1.05, and the reaction formula is:

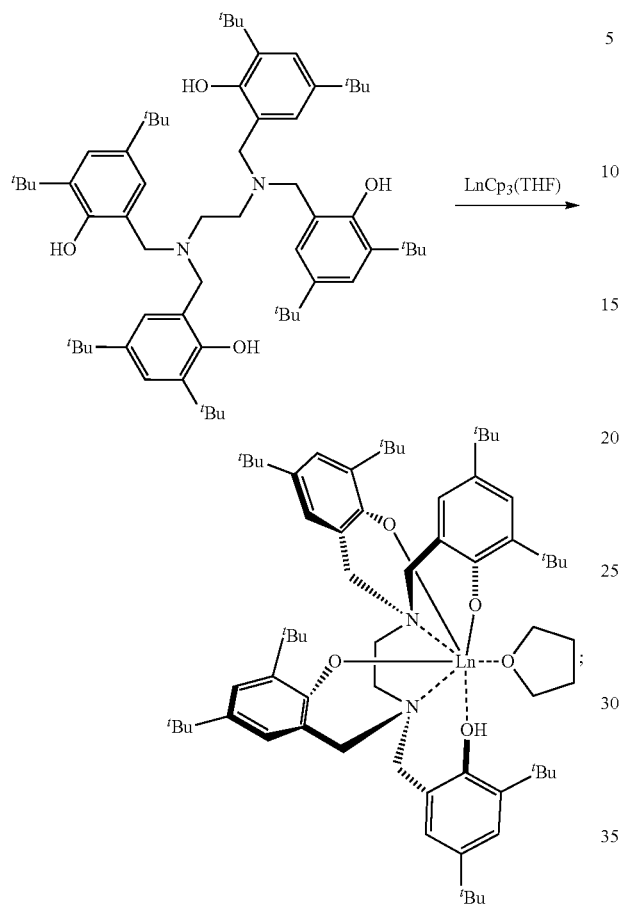

and 3) synthesis of bridged tetra(phenolate) rare earth-zinc heterobimetallic compound LnZnL(THF): reacting a solution of diethyl zinc in hexane or toluene with a solution of LnL(THF) in tetrahydrofuran at −5-50° C. for 8-12 h in the absence of water and oxygen, to obtain the bridged tetra(phenolate) rare earth-zinc heterobimetallic compound LnZnL(THF), wherein the molar ratio of diethyl zinc to LnL(THF) is 1:1-1.05:1, and the reaction formula is:

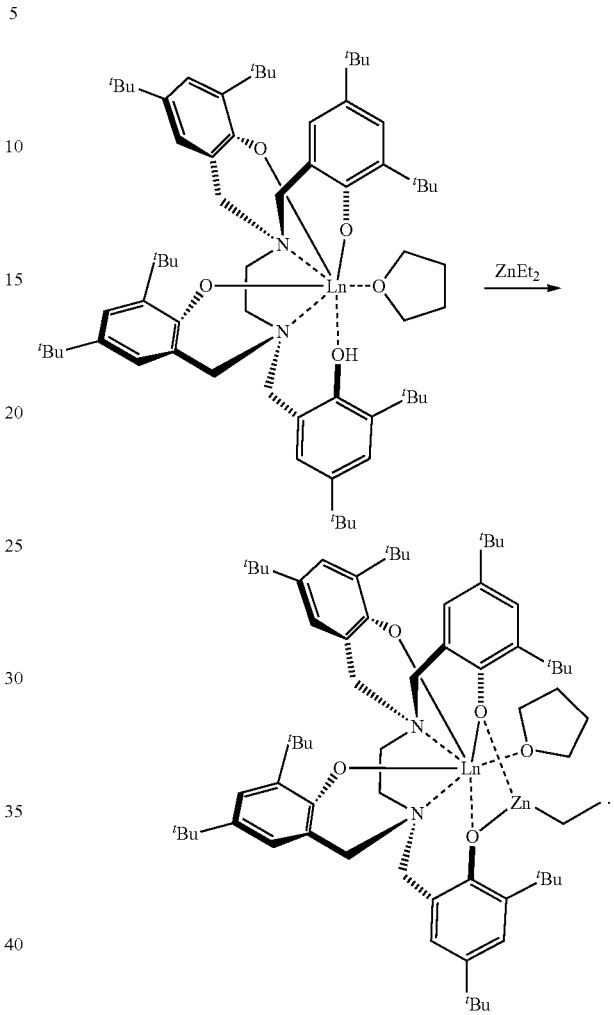

* * * * *